(12) United States Patent
Kheradvar et al.

(10) Patent No.: US 10,617,543 B2
(45) Date of Patent: Apr. 14, 2020

(54) DELIVERY SYSTEM FOR TRANSCATHETER DETACHMENT OF A STENT FROM THE DELIVERY DEVICE

(71) Applicant: The Regents of the University of California, Oakland, CA (US)

(72) Inventors: Arash Kheradvar, Irvine, CA (US); Gregory S. Kelley, Santee, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 237 days.

(21) Appl. No.: 15/111,482

(22) PCT Filed: Jan. 14, 2015

(86) PCT No.: PCT/US2015/011473
§ 371 (c)(1),
(2) Date: Jul. 13, 2016

(87) PCT Pub. No.: WO2015/109027
PCT Pub. Date: Jul. 23, 2015

(65) Prior Publication Data
US 2016/0331566 A1   Nov. 17, 2016

Related U.S. Application Data

(60) Provisional application No. 61/927,377, filed on Jan. 14, 2014.

(51) Int. Cl.
*A61F 2/95* (2013.01)
(52) U.S. Cl.
CPC ........ *A61F 2/95* (2013.01); *A61F 2002/9505* (2013.01); *A61F 2002/9511* (2013.01); *A61F 2002/9517* (2013.01)

(58) Field of Classification Search
CPC ...... A61F 2002/9505; A61F 2002/9511; A61F 2002/9517; A61F 2/95; A61F 2002/9522;
(Continued)

(56) References Cited

U.S. PATENT DOCUMENTS

| 5,534,007 A | 7/1996 | St. Germain et al. |
| 7,329,275 B2 | 2/2008 | Yee |

(Continued)

OTHER PUBLICATIONS

PCT International Search Report and the Written Opinion of the International Searching Authority for PCT/US2015/011473; dated Sep. 16, 2015.

(Continued)

*Primary Examiner* — Kathleen S Holwerda
*Assistant Examiner* — Brooke Labranche
(74) *Attorney, Agent, or Firm* — Tope-McKay & Associates (57) ABSTRACT

Described is an apparatus for transcatheter detachment of a stent from a delivery device. A braided suture with an opening is inserted through a restraining hole in a glide (the opening is secured on one side by a knot or a series of knots) and a release line is inserted through the braided suture opening. The braided suture is thus prevented from pulling through the restraining hole while the release line is through the opening. The braided suture is free to pass through the restraining hole after the release line is pulled out of the opening and thereafter pulled free of stent holes formed through a stent, thereby detaching the stent at a desired location.

12 Claims, 9 Drawing Sheets

(58) Field of Classification Search
CPC . A61F 2002/962; A61F 2/2427; A61F 2/2439
See application file for complete search history.

(56) References Cited

U.S. PATENT DOCUMENTS

| | | |
|---|---|---|
| 2006/0142836 A1* | 6/2006 | Hartley .................... A61F 2/07 623/1.11 |
| 2006/0190070 A1 | 8/2006 | Dieck et al. |
| 2012/0016469 A1 | 1/2012 | Salahieh et al. |
| 2012/0022633 A1 | 1/2012 | Olson et al. |
| 2012/0303109 A1 | 11/2012 | Okuma |
| 2013/0310923 A1 | 11/2013 | Kheradvar et al. |
| 2014/0277414 A1 | 9/2014 | Kheradvar |

OTHER PUBLICATIONS

Arash Kheradvar et al. "Proof of concept of FOLDAVALVE, a novel 14 Fr totally repositionable and retrievable transcatheter aortic valve" EuroIntervention, Mar. 16, 2015, pp. 1-7.
International Preliminary Report on Patentability for PCT/US2015/011473; dated Jul. 28, 2016.

\* cited by examiner

DELIVERY SYSTEM FOR TRANSCATHETER DETACHMENT OF A STENT FROM THE DELIVERY DEVICE

CROSS-REFERENCE TO RELATED APPLICATIONS

This application claims priority to U.S. Provisional Application No. 61/927,377, filed on Jan. 14, 2014, entitled, "Apparatus for Transcatheter Detachment of a Stent From The Delivery Device."

BACKGROUND OF THE INVENTION (1) Field of Invention

The present invention relates to percutaneously-delivered stents and, more particularly, to associated stent delivery systems for transcatheter delivery and implantation.

(2) Description of Related Art

This invention is related to the field of stents. During transcatheter implantation of stents (e.g., valve housings or other stent-related deliveries) optimal positioning and placement of the stent is crucial for treatment success and optimal outcome. Once the stent has been optimally positioned it is equally important that it remains optimally positioned as the stent is being detached from the delivery system without undue stress or motion during detachment. Typical stent delivery systems suffer in that they may inadvertently alter the position of the stent during detachment.

Thus, a continuing need exists for a stent delivery system for transcatheter delivery and implantation that minimizes stress and motion of the stent during detachment.

SUMMARY OF INVENTION

The present invention relates to percutaneously-delivered stents and, more particularly, to associated stent delivery systems for transcatheter delivery and detachment of a stent. The delivery system includes a glide having a plurality of restraining holes therethrough. A plurality of draw lines are also included. Each draw line has an opening formed therethrough and is adapted to pass through a stent hole in a stent and thereafter through a restraining hole in the glide. A release line is included that has a distal end and a proximal end. The distal end of the release line is adapted to pass through the openings of the draw lines and affix a stent with the glide, whereby upon implantation, a user can pull on the proximal end of the release line, which pulls the release line from the draw lines to allow the draw lines to be drawn from the stent, thereby detaching the stent at a desired location.

In another aspect, each of the draw lines is formed of a braided suture.

In yet another aspect, the glide is formed as a cylindrical barrel, such that the draw lines extend from a delivery device and through the glide and out of a distal end of the glide, with the draw lines passing through the stent and into the glide through the restraining holes in the glide.

In another aspect, each braided suture is formed of at least three braided strands and has a distal end, with one or more knots formed proximal the distal end.

In yet another aspect, each of the braided strands is formed of a plurality of filaments and the opening in each draw line is formed by piercing through and separating the filaments such that approximately half of the filament reside on each side of the opening.

In another aspect, the release line has a diameter and each of the restraining holes in the glide have a diameter, such that the diameter of the release line is greater than the diameter of the restraining holes in the glide.

In yet another aspect, the draw lines extend substantially parallel with the release line, with the draw lines thereafter extending through the glide.

Finally, as can be appreciated by one in the art, the present invention also comprises a method for forming and using the invention described herein. For example, the method comprises acts of pulling a release line, such that upon pulling the release line, the release line is pulled free of openings formed through a plurality of draw lines, thereby releasing the draw lines from a glide; and drawing on the draw lines to pull the draw lines from restraining holes in the glide and stent holes in the stent, thereby detaching the stent at a desired location.

BRIEF DESCRIPTION OF THE DRAWINGS

The objects, features and advantages of the present invention will be apparent from the following detailed descriptions of the various aspects of the invention in conjunction with reference to the following drawings, where:

FIG. 3A-A is an expanded view of FIG. 3A, illustrating a multiple filament structure of the strands;

DETAILED DESCRIPTION

The present invention relates to percutaneously-delivered stents and, more particularly, to associated stent delivery systems for transcatheter delivery and implantation. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Description

Described is a stent delivery system for transcatheter delivery and implantation. The stent delivery system provides an improved system for stent detachment from the delivery device, such as but not limited to a delivery system of a transcatheter heart valve or any other stent. This invention addresses the need for improved detachment of the stent from the delivery system to minimize interactional forces between the delivery device and the stent during detachment (to minimize inadvertent movement of the stent during detachment). In doing so, the detachment points, in one aspect, are located on the stent (so that detachment is of relatively short duration), and are released nearly simultaneously (to minimize inadvertent movement).

Figure 1:
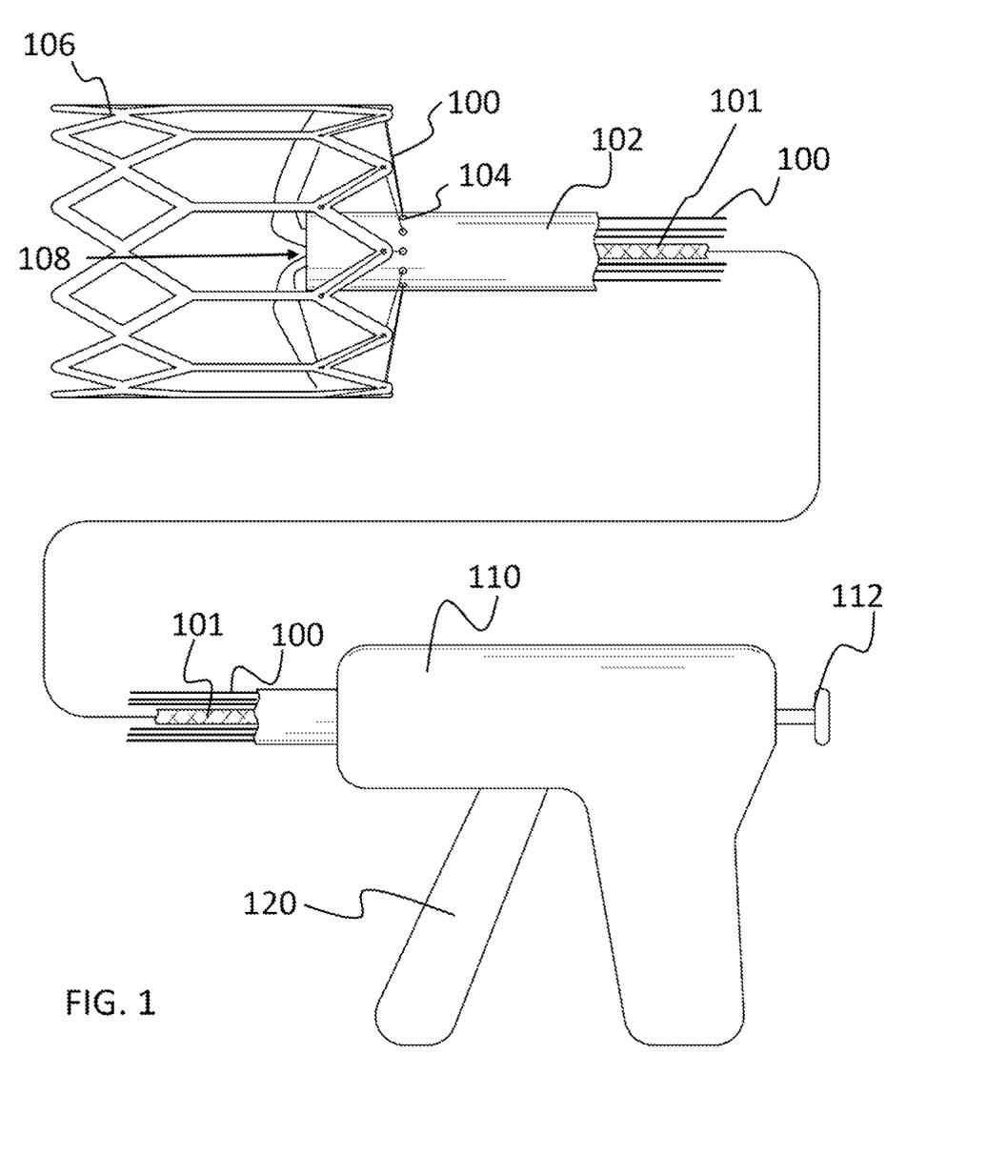
FIG. 1 is an illustration depicting draw lines extending substantially parallel with a release line and through a stent and to a delivery device according to the principles of the present invention.

As shown in FIG. 1, the stent delivery system includes a plurality of draw lines 100 (e.g., twelve lines or any other desired number) that extend from a handle 110 substantially parallel with a release line 101 (internal of a restraining part (i.e., glide 102)) and out of distal end 108 of glide 102, through a stent 106 and back through restraining holes 104 in the glide 102. Note that the delivery system includes a restraining part that is operable to selectively restrain the draw lines 100 during delivery. However, the restraining part also needs to be formed to allow the draw lines 100 to glide out of the said part and, as such, is hereinafter referred to as the glide 102.

Figure 2A:
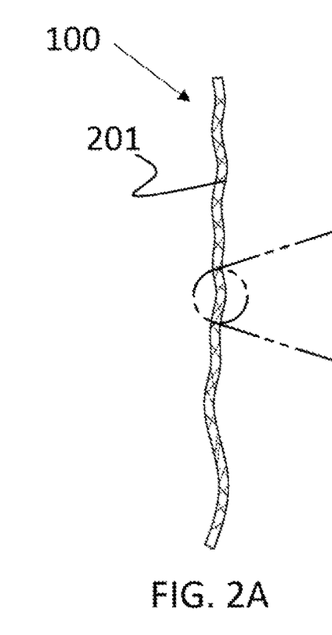
FIG. 2A is an illustration of a braided suture.
Figures 2B, 2C:
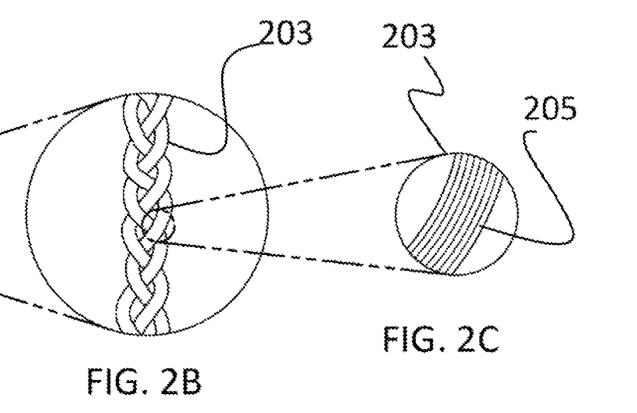
FIG. 2B is an expanded view of FIG. 2A, illustrating a three-stand braided suture and strands.
FIG. 2C is an expanded view of FIG. 2B, illustrating a multiple filament structure of the strands.

The draw lines 100 in effect keep the stent 106 affixed with the glide 102 during delivery. They can also be selectively drawn (i.e., pulled) to turn the stent 106 as desired during delivery and implantation. The draw lines 100 can be free on their proximal ends, or desirably, connected with a draw line trigger 120 or other suitable component of the delivery device 110. The release line 101 is connected to a handle release trigger 112 or knob (or other suitable device for drawing the release line 101) of the delivery device 110. The draw lines 100 can be pulled to hold the stent 106 tight against the glide 102 during delivery. When at the desired delivery site, the release line 101 is pulled, which in turn releases the draw lines 100, allowing the draw lines 100 to be pulled out of the stent 106 and, thereby, release the stent 106 at the desired location These components are described in further detail below. It should be noted that the draw lines 100 can be formed of any material that allows for formation or fixation of an opening (an example of which described below with respect to the opening 200). As a non-limiting example, the draw lines 100 can be formed of monofilaments (e.g., nylon) that are pierced with a needle or other device to form an opening therethrough. FIG. 2A, for example, illustrates another non-limiting example of a draw line 100. In this example and as shown in FIG. 2A, one or more draw lines 100 are formed of a braided suture 201 to provided additional strength. To be contrasted with the example above where each draw line is a single monofilament, in this aspect, each draw lines is braided suture 201 formed of many filaments. For example, each braided suture 201 (i.e., draw line) is formed of any suitably braidable filaments, non-limiting examples of which include nylon, Polytetrafluoroethylene (PTFE), Ultra-high-molecular-weight polyethylene (UHMWPE), polyester, and Polyether ether ketone (PEEK). For further understanding, FIG. 2A is an illustration of the braided suture 201. FIG. 2B is an expanded view of FIG. 2A, showing the braided suture 201 as a three-strand braided structure formed of at least three strands 203. Further, FIG. 2C is an expanded view of FIG. 2B, illustrating multiple monofilaments 205 that are aliened to form each of the individual strands 203.

Figure 2D:
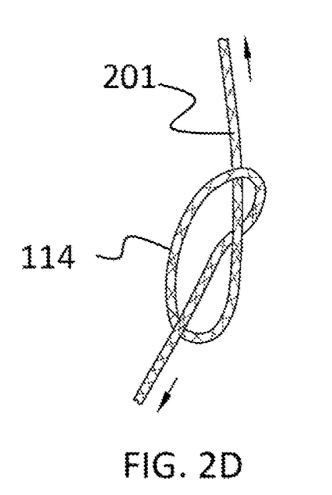
FIG. 2D is an illustration of a knot, untightened.
Figure 2E:
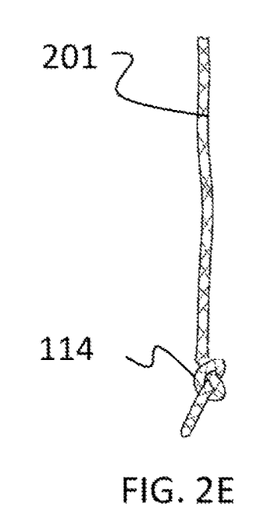
FIG. 2E is an illustration of a knot, tightened.

To provide the delivery and detachment features herein, the braided suture 201 includes at least one knot (and possibly multiple knots). For example and as shown in FIG. 2D, the braided suture 201 can be twisted into a first knot 114 (and additional knots as desired), a tightened version of which is shown in FIG. 2E. As can be appreciated by those skilled in the art, there are many techniques for tying a knot, one of which is illustrated in FIGS. 2D and 2E; however, the invention is not intended to be limited thereto as the knot(s) can be formed using any suitable technique, another non-limiting example of which is illustrated in FIGS. 3A through 3D.

Figure 2F:
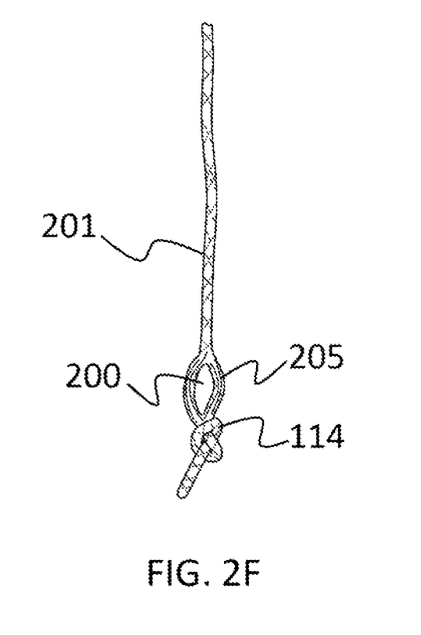
FIG. 2F is an illustration of an opening created in the braided suture by piercing between monofilaments, close to but proximal of the knot (as shown in FIG. 2E)

It is desirable that the suture knots are kept minimal in profile so that they pass freely through size constraining features (such as the restraining holes in the glide and the stent holes in the stent). It is also desirable that each braided suture is as uniformly pliable as practical so that the braided sutures slide freely through and around surfaces and edges (such as the stent). It is also desirable that the braided sutures and knot(s) provide adequate strength, e.g., to secure the stent (such as but not limited to a stented heart valve) in a collapsed state. A desired aspect is described in which the profile (size) of the suture knot(s) is/are kept minimal, in which changes to the braided suture pliability is minimalized, and in which the braided suture knots provide adequate strength. As a non-limiting example, the suture knot profile illustrated in FIGS. 2D, 2E, and 2F is approximately three times the braided suture profile, or, since the braided suture profile is approximately three times the strand profile, approximately nine times the strand profile.

In another aspect and as shown in FIGS. 3B through 3E (and 4A through 4E, 5A and 5B), the knot profile(s) are approximately five times the strand profile. An objective of a desired embodiment of the knot/braid pattern is illustrated in FIGS. 3A through 3E is to maintain braided suture pliability with minimal profile and adequate strength.

As described in further detail below, to provide the draw and detachment features, the braided suture 201 needs an opening formed therethrough. FIG. 2F, for example, provides an illustration of an opening 200 created in the braided suture 201 by piercing between monofilaments 205. The opening 200 can be formed at any suitable location; however, desirably, the opening 200 is formed proximal to the first knot 114 with approximately half of the monofilaments 205 spread to each side of the opening 200.

Figure 3A:
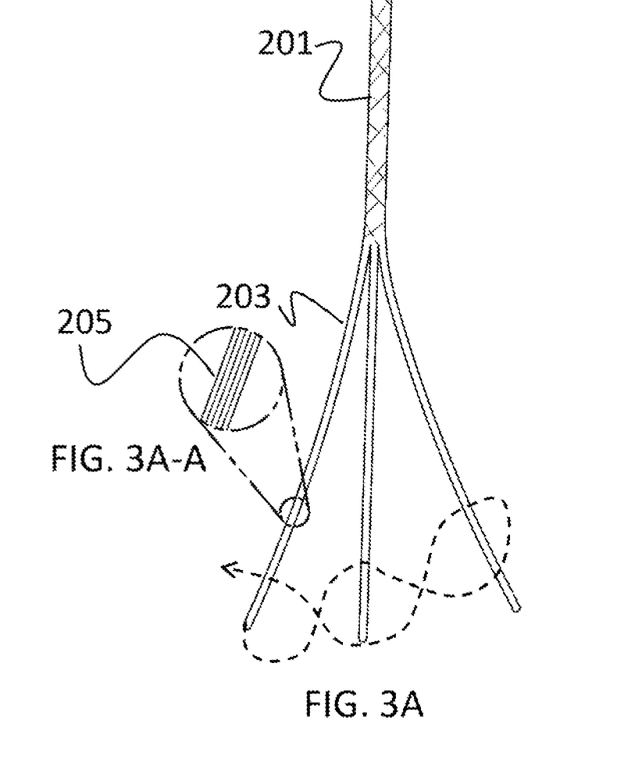
FIG. 3A is an illustration of a braided suture where the strands have been separated at one end.
Figure 3B:
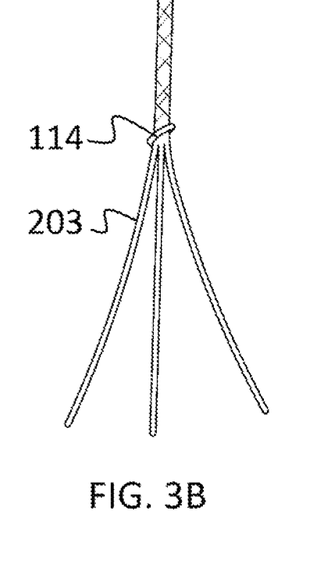
FIG. 3B is an illustration of a knot formed by looping strand one around the other two strands and tying a knot close to the point at where the strands have been separated.
Figure 3C:
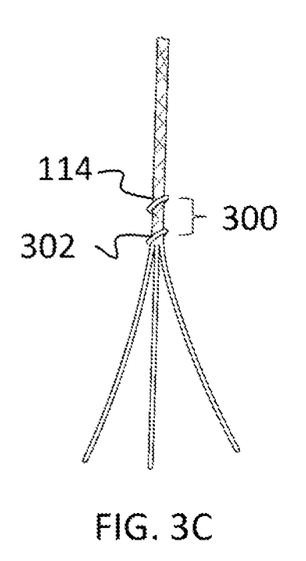
FIG. 3C is an illustration of braiding distal from the knot illustrated in FIG. 3B for a distance and then tying a second knot by looping strand two around the other two strands and tying a knot.
Figure 3D:
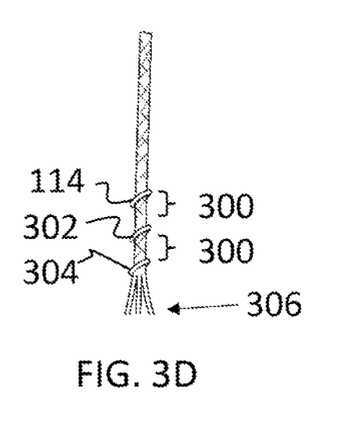
FIG. 3D is an illustration of braiding distal from the knot in FIG. 3C for a distance and then tying a third knot by looping strand three around the other two strands and tying a knot, further depicting the strands as being cut a short distance distal of the third knot.

As noted above, another example of a knot tying process is illustrated in FIGS. 3A through 3D. For example, FIG. 3A illustrates the braided suture 201 where the individual strands 203 have been separated at one end. As noted above and as illustrated in FIG. 3A-A (which is an expanded view of FIG. 3A), the individual strands 203 are formed of multiple mono-filaments 205. In this aspect and as shown in FIG. 3B, the knot is formed by looping a first strand around the other two strands and tying the knot 114 close to the point at where the strands 203 have been separated. After the first knot 114 is tied, it may be desirable to tie as few additional knots, as shown in FIGS. 3C and 3D. Thus, the strands can braided at the distal end for a desired distance 300 with a second knot 302 being tied, for example, by looping a second strand around the other two strands and tying the second knot 302. A desired distance 300 is the span of 4 or 5 braid crossings for one preferred embodiment but may be chosen differently to suit another aspect, which is important because this helps maintain suture pliability so that the braided sutures slide freely through and around surfaces and edges (such as the stent) while also providing adequate knot strength.

As noted above, any desired number of knots can be incorporated into the braided suture 201. However, desirably, three knots are included so that each of the three strands is knotted and each strand contributes to the overall strength. For example, FIG. 3D is an illustration of braiding the strands distal from the second knot 302 in FIG. 3C for a distance 300 and then tying a third knot 304 by looping a third strand around the other two strands and tying the third knot 304. In this non-limiting example, the strands are illustrated as being cut 306 a short distance distal of the third knot 304.

The braided suture 201 is less pliable at the knot(s) than in the braided lengths and less pliable at larger knots than at smaller knots. Thus, minimal knot size serves to minimize the change in braided suture pliability. The braided section between knots serves to spread the change in braided suture pliability over a length while simultaneously maintaining adequate knot slip strength. In other words, it is preferred that the discontinuity in pliability is smaller (in both scale and in physical length) and spread out in length rather than larger (in both scale and physical length). The triplicate knot pattern (as shown in FIG. 3D) secures each strand and provides adequate strength. In another aspect, the braided suture 201 is approximately the size of a human hair (i.e., in diameter or width), the strands are approximately one third the size of a human hair and the individual filaments are much smaller. Of course this is only illustrative and other knot/braid configurations are possible.

Figure 3E:
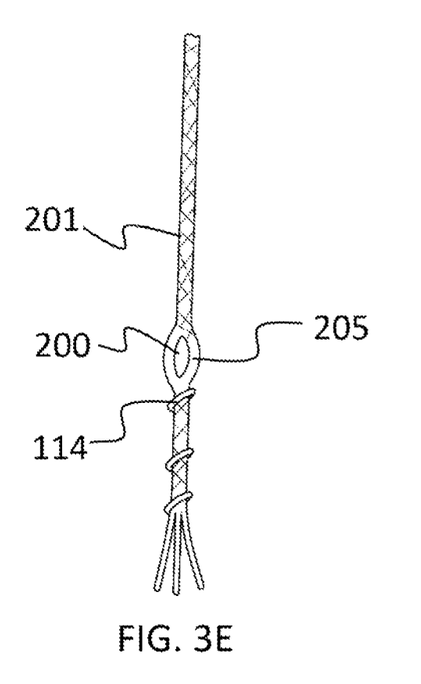
FIG. 3E is illustration of an opening created in the braided suture by piercing between monofilaments, close to but proximal of the first knot.

As was the case above and as shown in FIG. 3E, the opening 200 is created in the braided suture 201 by piercing between monofilaments 205, close to but proximal of the first knot 114. Desirably, approximately one half of the monofilaments are separated to each side of the opening 200. After the opening 200 is formed, the release line (depicted as element 101 in FIG. 1) is positioned through the opening 200.

Figure 4A:
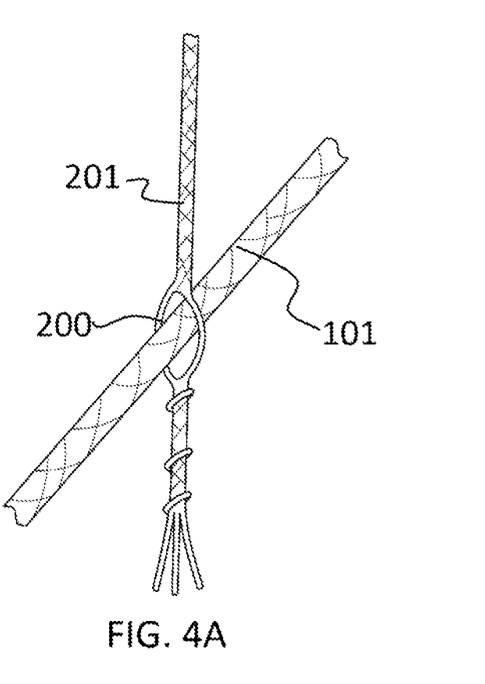
FIG. 4A is an illustration depicting positioning of a second, larger size suture (i.e., release line) through the opening of the braided suture depicted in FIG. 4E.
Figure 4B:
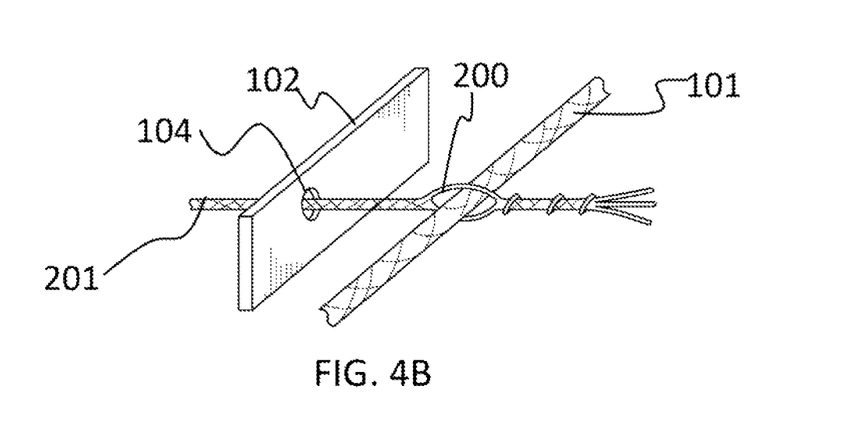
FIG. 4B is an illustration depicting a restraining part with a hole, the braided suture through the hole, and the release line through the braided suture opening (as illustrated in FIG. 4B, the release line is larger than the hole in the restraining part, alternatively the width of the release line may be smaller than the hole where the release line is sufficiently stiff to resist being pulled into the hole)

For example and as shown in FIG. 4A, the release line 101 (e.g., a second, larger-size suture) is positioned through the opening 200 of the braided suture 201 structure. The release line 101 is formed of any suitably durable material, a non-limiting example of which includes nylon, UHMWPE, polyester suture, stainless steel wire, super elastic nitinol wire. As shown in FIG. 4B, the braided suture 201 and release line 101 are used in conjunction with a restraining part (e.g., the glide 102). The restraining part or glide 102 serves to provide a structure against which the release line 101 is restrained, thereby allowing a tensile force to be placed on the draw lines. As shown, the glide 102 includes at least one restraining hole 104 therethrough. The braided suture 201 passes through the restraining hole 104, with the larger release line 101 passing through the opening 200 of the braided suture 201. Notably, the diameter of the release line 101 may be greater than the restraining hole 104 in the glide 102 or the release line may be sufficiently stiff which prevents the release line 101 from being pulled through the restraining hole 104 when the braided suture 201 is being drawn taut.

Figure 4C:
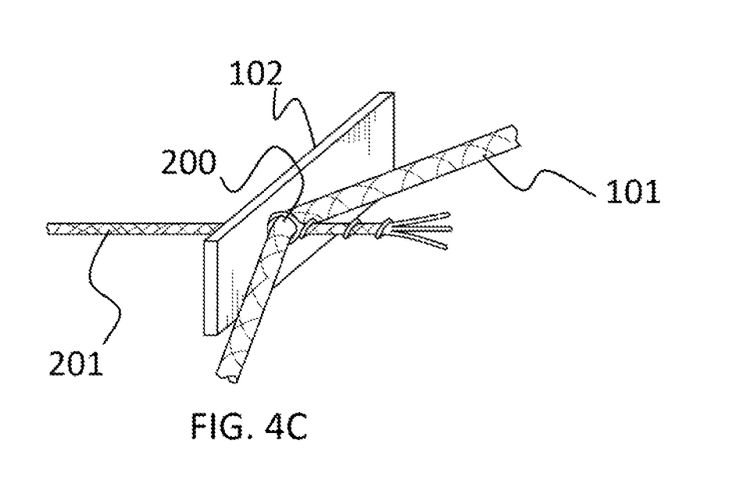
FIG. 4C is an illustration similar to that of FIG. 4B, depicting the braided suture under tension.
Figure 4D:
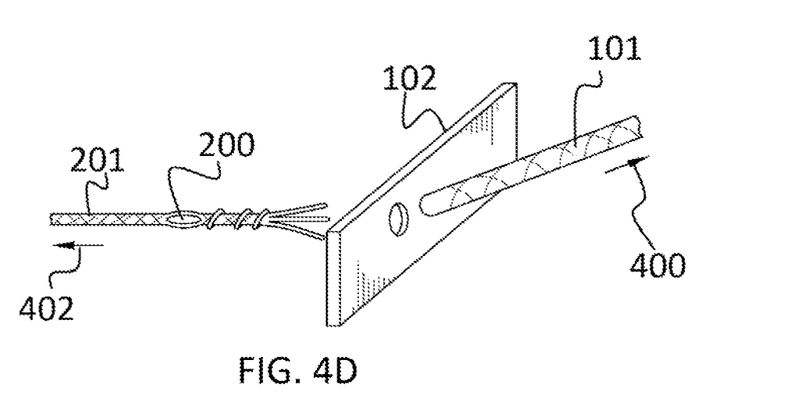
FIG. 4D is an illustration depicting the larger release line being pulled out of the braided suture, the braided suture (being under tension) slips out of the restraining part.
Figure 4E:
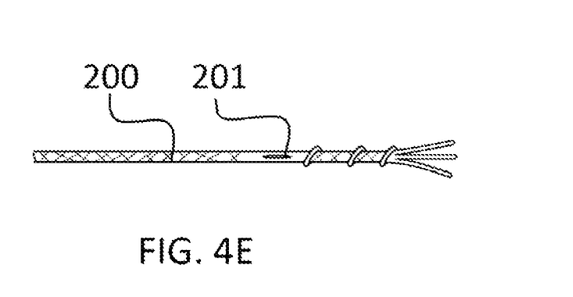
FIG. 4E is an illustration depicting collapse of the opening in the braided suture.

FIG. 4C is an illustration similar to that of FIG. 4B, depicting the braided suture 201 structure under tension when being pulled as a draw line. Notably, the stent is affixed with the glide 102 via the draw line (braided suture 201), with the braided suture 201 affixed within the glide 102 since the release line 101 is passing through the opening 200. When the stent is at the desired implant location, a user can pull on the release line 101 (using the delivery device). As shown in FIG. 4D, as the release line 101 is pulled 400 toward the delivery device, the release line 101 is pulled out of the opening 200 in the braided suture 201. With the release line 101 drawn from the opening 200, the braided suture 201 is free to be drawn 402 free of the glide 102 and, thereafter, drawn from the stent and back into the distal end of the glide 102. As can be appreciated by those skilled in the art and as shown in FIG. 4E, the opening 200 is easily collapsed (as depicted) to allow the suture 201 to be drawn from the glide and stent to allow for detachment from the stent.

Figure 5A:
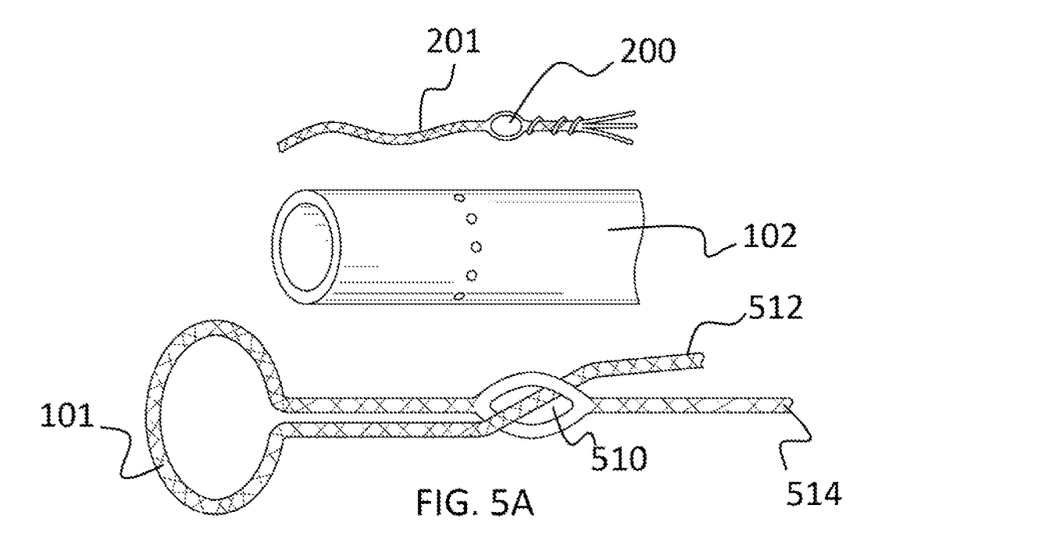
FIG. 5A is an illustration depicting components of the delivery system, including a draw line (e.g., braided suture), restraining part (i.e., glide), and larger suture (i.e., release line)

Thus and as depicted in FIG. 5A, the delivery system includes at least a draw line (e.g., a plurality of braided suture(s) 201), a restraining part (e.g., a glide 102), and a larger suture (i.e., a release line 101). The release line 101, in one aspect, can be formed into include a release line opening 510 (e.g., by piercing the release line 101 or through any other suitable technique for forming an opening in a line). The release line 101 also includes a distal end 512 and a proximal end 514 that continues to the delivery device 110 (as shown in FIG. 1). The use of the release line opening 510 provides a technique for lightly fixing the distal end 512 of the release line 101 so that it does not inadvertently move out of the draw lines (e.g., braided sutures 201) prematurely. When pulling the proximal end 514 of the release line 101 (via the handle release trigger), the distal end 512 of the release line 101 slides out of the release line opening 510 and then out of the braided suture openings 200.

Figure 5B:
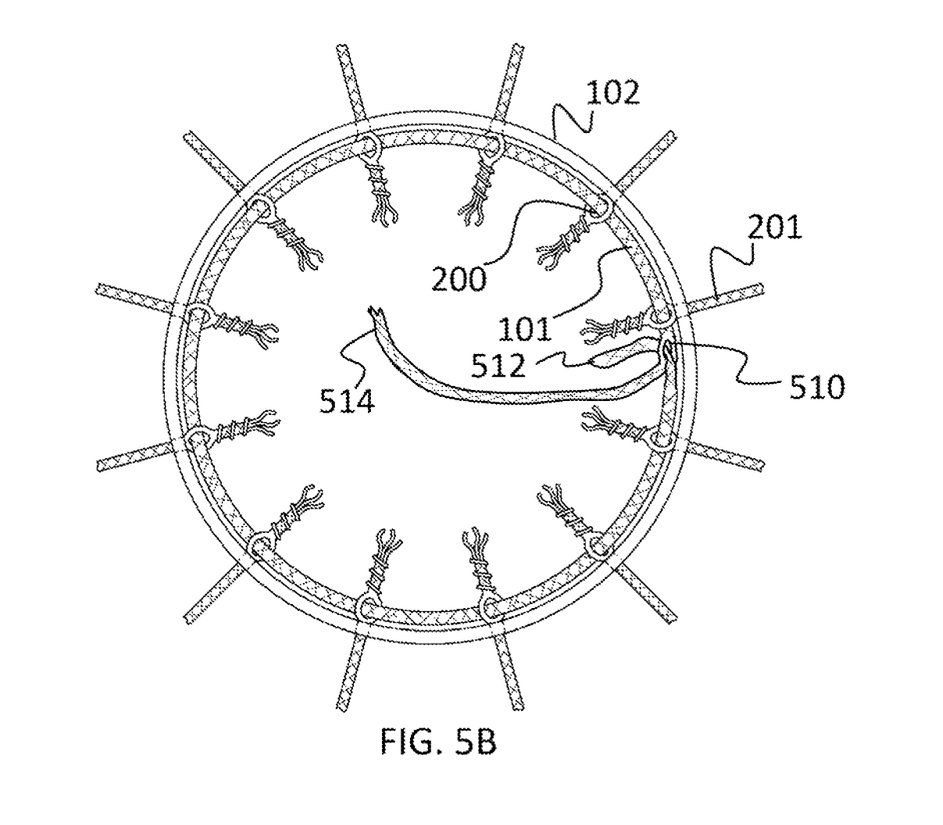
FIG. 5B is an illustration depicting a distal end-view, showing draw lines inserted through the glide, with a release line positioned through openings in the draw line.

As noted above and as further illustrated in the distal-end view of FIG. 5B, the braided sutures 201 are affixed with the glide 102 by the release line 101 which passes through openings 200 in the braided sutures 201. Also as shown, the distal end 512 of the release line 101 is passed through the release line opening 510, with the proximal end 514 of the release line 101 passing through the glide 102 and toward the delivery device.

Figure 5C:
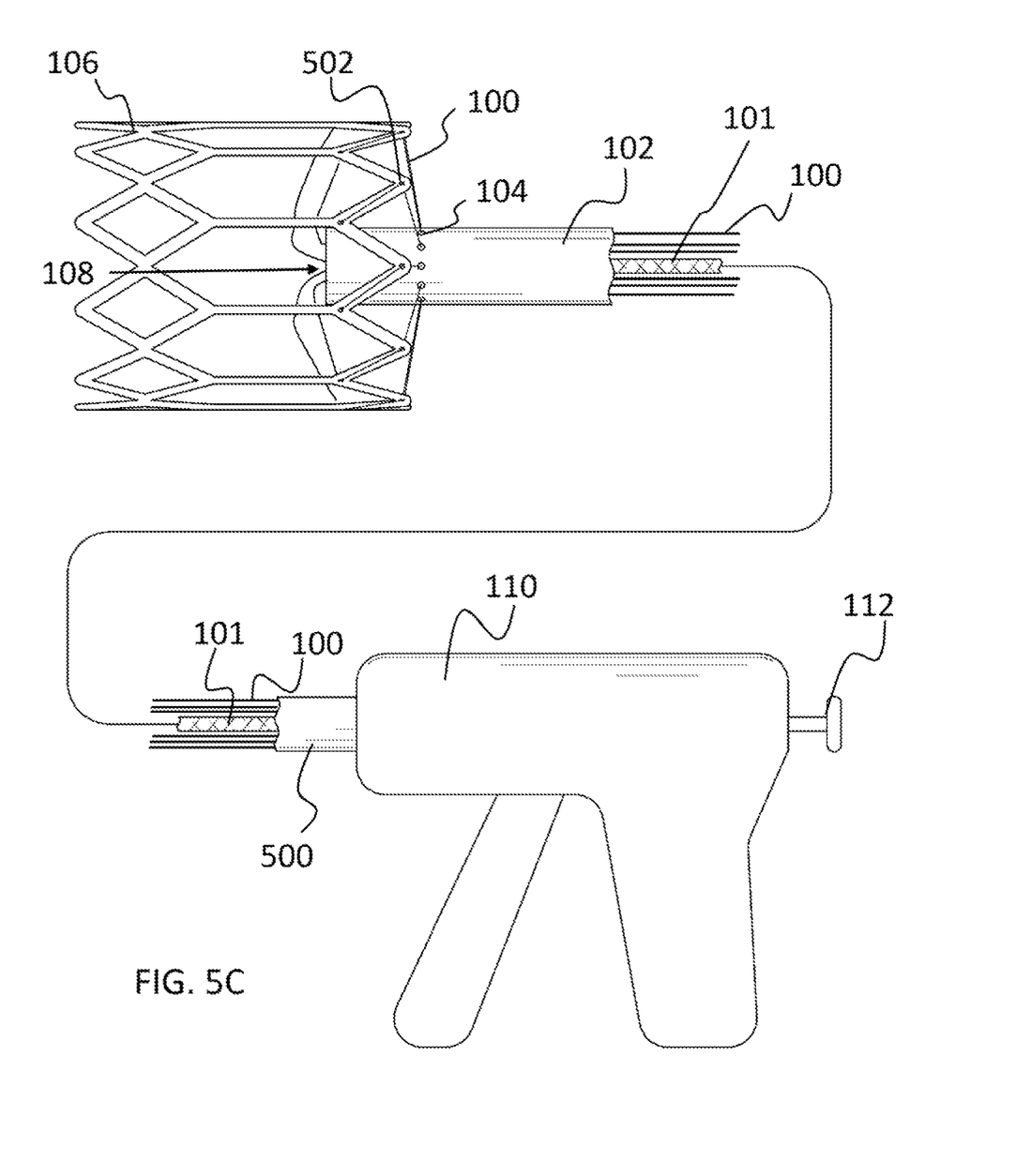
FIG. 5C is an illustration depicting draw lines extending substantially parallel with a release line and through a stent and to a delivery device according to the principles of the present invention.

For clarity, the delivery system described herein can be implemented with any suitable stent delivery device 110, a non-limiting example of which is shown in FIG. 5C. A non-limiting example of an off the shelf delivery device is that sold by Edwards Lifesciences Corporation, and Medtronic CoreValve®. The glide 102 (i.e., restraining party can be used in conjunction with the sheath 500 of such a delivery device 110. Also projecting from the delivery device 110 are the draw lines 100 (e.g., braided sutures 201) and release line 101. For clarity and as noted above, the braided sutures 201 are provided as a non-limiting example of suitable draw lines 100 according to the principles of the present invention and, as such, are terms that are used herein interchangeably. The draw lines 100 continue through the glide 102 and out of the distal end 108 of the glide 102. The glide 102 is any suitable device that is operable for restraining the draw lines 100 as described. For example, the glide 102 is a cylindrically-shaped barrel or tube. The draw lines 100 continue out of the glide 108 and through the various stem holes 502 in the stent 106. After passing through one or more stent holes 502 in the stent 106, the draw lines 100 continue through restraining holes 104 in the glide 102 and back into the glide 102. Inside the glide 102 (as shown in FIG. 5B), the draw lines 100 are affixed within the glide 102 due to the release line 101 passing through the openings 200 in the draw lines 100 (i.e., braided sutures 201). When a user pulls the release line 101 with the delivery device 110, the release line 101 is pulled out of the openings 200 in the draw lines 100, which allows the draw lines 100 to be pulled out of the restraining holes 104 in the glide 102 and, also, out of the stent holes 502 in the stem 106, thereby detaching entirely from the stent 106.

What is claimed is:

1. A delivery system for transcatheter delivery and detachment of a stent, comprising: a glide, the glide having a cavity terminating in a distal end of the glide, the glide also having a plurality of restraining holes formed through the glide; a plurality of draw lines, each draw line having an opening formed therethrough, and wherein each draw line passes through the cavity and from the distal end of the glide, and thereafter through a stent hole in a stent and through a restraining hole in the glide such that the opening of each draw line resides within the cavity of the glide; and a release line having a distal end and a proximal end, the distal end of the release line passing through the openings of the draw lines to affix the plurality of draw lines to the distal end of the glide and, thereby, affix a stent with the glide, whereby upon implantation, a user can pull on the proximal end of the release line, which pulls the release line from the draw lines to allow the draw lines to be drawn from the stent, thereby detaching the stent at a desired location.

2. The delivery system as set forth in claim 1, wherein each of the draw lines is formed of a braided suture.

3. The delivery system as set forth in claim 2, wherein the glide is formed as a cylindrical barrel, such that the draw lines extend from a delivery device and through the glide and out of the distal end of the glide, with the draw lines passing through the stent and into the glide through the restraining holes in the glide.

4. The delivery system as set forth in claim 3, wherein each braided suture is formed of at least three braided strands and has a distal end, with one or more knots formed proximal the distal end of each braided suture.

5. The delivery system as set forth in claim 4, wherein each of the braided strands is formed of a plurality of filaments and wherein the opening in each draw line is formed by piercing through and separating the filaments such that approximately half of the filaments reside on each side of the opening.

6. The delivery system as set forth in claim 5, wherein the release line has a diameter and each of the restraining holes in the glide have a diameter, such that the diameter of the release line is greater than the diameter of the restraining holes in the glide.

7. The delivery system as set forth in claim 6, wherein the draw lines extend substantially parallel with the release line with the draw lines thereafter extending through the glide.

8. The delivery system as set forth in claim 2, wherein each braided suture is formed of at least three braided strands and has a distal end, with one or more knots formed proximal the distal end of each braided suture.

9. The delivery system as set forth in claim 8, wherein each of the braided strands is formed of a plurality of filaments and wherein the opening in each draw line is formed by piercing through and separating the filaments such that approximately half of the filaments reside on each side of the opening.

10. The delivery system as set forth in claim 1, wherein the glide is formed as a cylindrical barrel, such that the draw lines extend from a delivery device and through the glide and out of the distal end of the glide, with the draw lines passing through the stent and into the glide through the restraining holes in the glide.

11. The delivery system as set forth in claim 1, wherein the release line has a diameter and each of the restraining holes in the glide have a diameter, such that the diameter of the release line is greater than the diameter of the restraining holes in the glide.

12. The delivery system as set forth in claim 1, wherein the draw lines extend substantially parallel with the release line with the draw lines thereafter extending through the glide.

* * * * *